United States Patent

Winslow et al.

Patent Number: 5,489,977
Date of Patent: Feb. 6, 1996

[54] PHOTOMERIC MEANS FOR MONITORING SOLIDS AND FLUORESCENT MATERIAL IN WASTE WATER USING A FALLING STREAM WATER SAMPLER

[75] Inventors: Gregory A. Winslow, Houston; Dale F. Brost, Sugar Land; Judith A. Newton, Houston, all of Tex.

[73] Assignee: Texaco Inc., White Plains, N.Y.

[21] Appl. No.: 104,705

[22] Filed: Aug. 11, 1993

[51] Int. Cl.⁶ .................................................. G01B 21/00
[52] U.S. Cl. ........................................... 356/73; 356/339
[58] Field of Search ............................. 356/72, 73, 339; 250/461.1

[56] References Cited

U.S. PATENT DOCUMENTS

| | | | |
|---|---|---|---|
| 3,849,654 | 11/1974 | Malvin | 356/246 |
| 3,917,945 | 11/1975 | Sema et al. | 250/461.1 |
| 4,426,154 | 1/1984 | Steen | 356/73 |
| 4,545,677 | 10/1985 | Chupp | 356/72 |
| 4,573,796 | 3/1986 | Martin et al. | 356/73 |
| 4,609,286 | 9/1986 | Sage, Jr. | 356/73 |
| 4,662,742 | 5/1987 | Chupp | 356/73 |
| 4,988,619 | 1/1991 | Pinkel | 356/73 |
| 5,047,963 | 9/1991 | Kosaka | 356/339 |
| 5,400,137 | 3/1995 | Winslow et al. | 356/318 |

OTHER PUBLICATIONS

"Flow Cytometry" 8127 Review of Scientific Instruments 55 (1984) Sep. No. 9 New York USA. John A Steinkamp.

*Primary Examiner*—F. L. Evans
*Assistant Examiner*—Robert Kim
*Attorney, Agent, or Firm*—James L. Bailey; Kenneth R. Priem; William J. Beard

[57] ABSTRACT

Turbidity and fluorescence measurements are taken simultaneously from a falling waste water stream in order to determine both the amount of solids and the amount of fluorescent material contained therein.

24 Claims, 2 Drawing Sheets

PHOTOMERIC MEANS FOR MONITORING SOLIDS AND FLUORESCENT MATERIAL IN WASTE WATER USING A FALLING STREAM WATER SAMPLER

BACKGROUND OF THE INVENTION

1. The Field of the Invention

The present invention relates to a method and apparatus for monitoring the concentration of solids and fluorescent materials in a flowing stream of waste water. In particular, the present invention involves the combined use of fluorescence and turbidity measurements to determine the suspended/dispersed solids and dissolved and dispersed fluorescent materials in flowing waste water.

2. The Prior Art

Waste water streams contain residual components whose discharge is controlled by government regulation. When waste waters are discharged into the environment, various government regulations require monitoring of the discharged water for contaminants, in particular for the solid and organic content. The results of such monitoring must be kept on file for government review. Depending on the type of waste water discharge, severe fines can be assessed when contaminant levels exceed maximum permissible limits. In an effort to comply with government regulations, industries involved with waste water discharge are searching desperately for analytical instruments that can measure water quality in real time. Real time measurements could then be used to prevent illegal discharges by providing early warnings of excessive contaminant levels.

Fluorescence is indicative of various organic contaminants whose presence is not desirable in discharged water streams. Turbidity is a measure of suspended particles in a water stream (whether due to organic or inorganic materials) and is a measure of water quality. The present invention involves using a single instrument to simultaneously measure the fluorescence and turbidity of a flowing water stream to determine the water quality of that stream. Although this invention would be very useful in monitoring water discharge streams from petroleum production, it would also be useful to monitor any sort of water stream.

A variety of instrumental methods have been tested for their ability to continuously monitor solids and fluorescent materials in various waste water streams. The following discussion emphasizes prior art in the area of monitoring residual oil in water streams resulting from petroleum production, but the present invention is not so limited.

Focused ultra-sonic beams have been used to determine the particle content and particle size distribution of suspended solids in water streams. This technique is incapable of detecting dissolved fluorescent materials and cannot distinguish between, for example, dispersed oil particles and other types of suspended solids of similar size.

Optical methods, based on turbidity (light scattering), absorption, and fluorescence, have also been applied. Turbidimetry can indicate the suspended particle content of a water stream by sensing light that is scattered from the particles as, for example, described in U.S. Pat. No. 3,309,956. Like the ultra-sonic technique, this method can only give a measurement of total particle content, and cannot distinguish between dispersed hydrocarbons and other types of suspended particles.

Absorption methods are based on the ability of aromatic hydrocarbons to absorb ultraviolet (UV) light in a manner that is proportional to concentration. These absorption methods are primarily useful for determining ppm levels of dissolved aromatic hydrocarbons. Total dissolved hydrocarbons can be estimated if the aliphatic hydrocarbons, which do not absorb light in the UV range, are in constant proportion to the UV absorbing aromatic hydrocarbons. Absorption techniques can also monitor dispersed hydrocarbons, but only if all the dispersed particles can be assumed to be 100% oil, and only if the particle size distribution is constant. Hybrid instruments are available which are capable of simultaneous absorption and turbidity measurements.

Fluorescence instruments also detect the aromatic components of petroleum hydrocarbons, but at much lower concentrations (parts-per-billion) than absorption instruments. Successful application of the fluorescence technique depends upon the same assumptions as discussed above for the absorption technique. This invention combines the techniques of turbidimetry and fluorescence into one water monitoring instrument that is not subject to fouling of the optical surfaces by contact with the water stream.

All known optical measurement techniques require a means for light to come into contact with the waste water, and for transmitted, scattered, or fluorescent light to be detected. A variety of flow cells with optical windows or fiber optic probes are available for this purpose. The optical windows of flow cells and fiber optic probes are subject to fouling in most waste water streams because the suspended particles in the system (hydrocarbons, bacteria, etc.) cling to the optical surfaces and interfere with the transmission of light.

For fluorescence and turbidity measurements, non-contact sample cells are also available. Light is directed through an open space to either a falling stream of water or a stabilized flowing water surface. Scattered or fluorescent light is then directed through an open space to a light detector. Fouling is eliminated because there is no direct contact between the water sample and the optical surfaces. One example of this optical arrangement is the Surface Scatter 6 Turbidimeter described in U.S. Pat. No. 3,309,956, for the measurement of highly turbid samples.

An example of the falling stream system for the measurement of fluorescence is an instrument by Sigrist (Sigrist, Ennetburgen, Switzerland). An example of the falling stream system for the measurement of turbidity is also made by Sigrist.

In the prior art there are many examples of photometers, but only one is found that is capable of measuring absorbance, turbidity, nephelometric light, and fluorescence at the same time. There are no examples of photometers which can make more than one type of measurement and are able to correct the fluorescence reading for error due to the turbidity of the sample, or which use a sample cell which will not be easily fouled by the waste water stream.

U.S. Pat. No. 4,060,327 shows a device which is capable of measuring only absorbance and turbidity. It also uses a sample cell which would be susceptible to fouling in a waste water stream.

The system described in U.S. Pat. No. 4,426,154 is a device which measures fluorescent light, scattered light, and/or absorbed light, however, it cannot measure nephelometric light.

Baker Instruments has a system which is capable of both absorbance and fluorescence measurements, but not nephelometric measurements.

U.S. Pat. No. 4,730,922 describes an instrument which is capable of measuring fluorescence, turbidity, absorbance, and nephelometry. However, a very crucial part of that instrument is the sample cell which would be very easily fouled by a waste water stream. Also, that invention does not seem to have the capability to correct the fluorescence measurement for the effects of turbidity.

SUMMARY OF THE INVENTION

The present invention uses a non-contact optical arrangement for simultaneously measuring fluorescence and turbidity using only one instrument. The optical arrangement is based upon a falling stream water sampler, in which light beams travel to and from the water sample without ever passing through an optical material that physically contacts the water sample. The subject instrument also has the means for correcting the fluorescence reading for the effect of turbidity.

BRIEF DESCRIPTION OF THE DRAWINGS

The present invention will now be described, by way of example, with reference to the accompanying drawings, in which.

DETAILED DESCRIPTION OF THE PREFERRED EMBODIMENT

Figure 1:
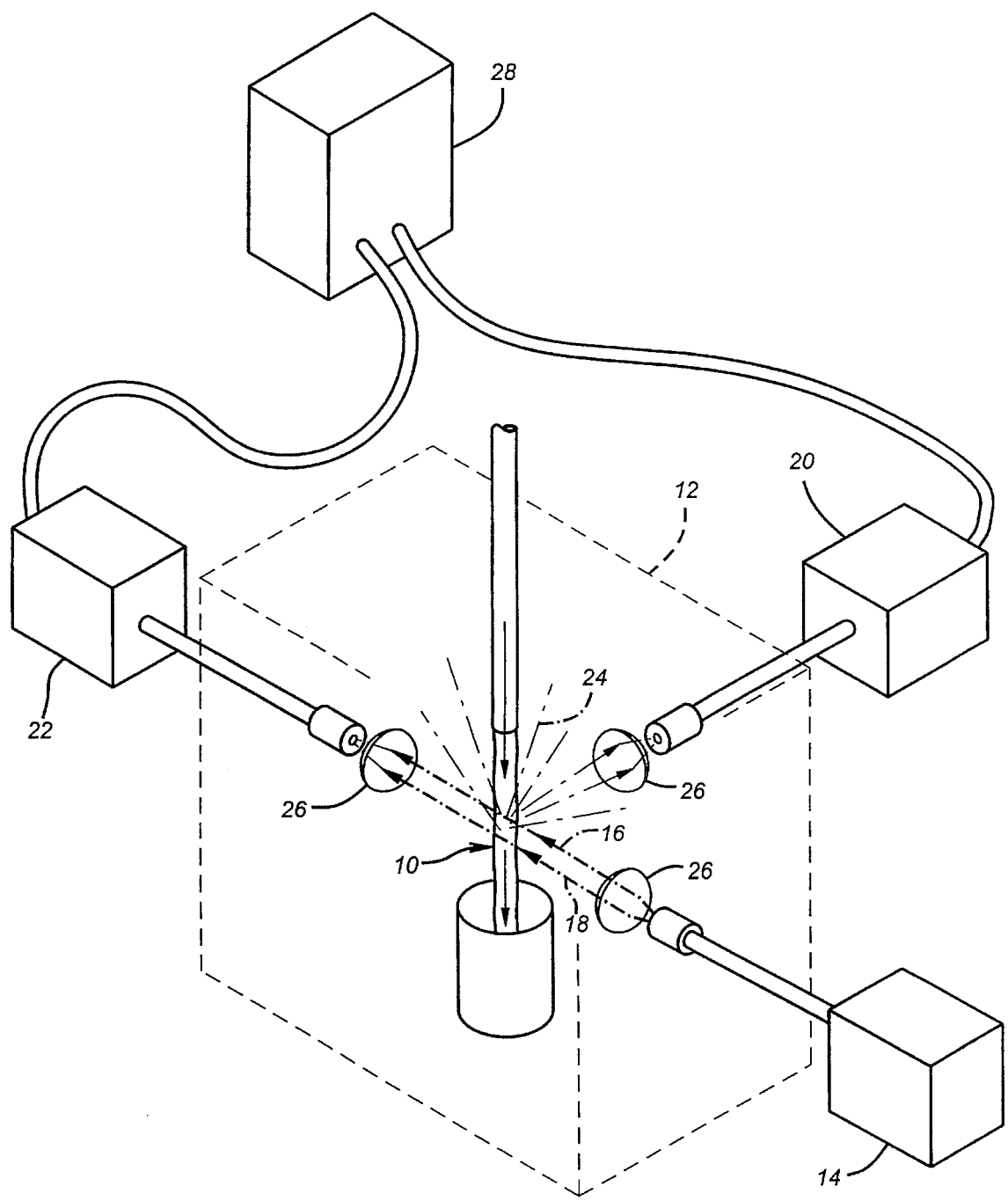
FIG. 1 is a schematic plan view of the present invention.

In the embodiment shown in FIG. 1, a water stream 10 to be studied passes in free fall through a sample cell 12. A dual-wavelength light source 14 directs two beams of light 16, 18 incident upon the water stream as it falls vertically through the cell 12. First and second detectors 20, 22 are positioned to detect light 24 emerging from the falling stream resulting from interactions between components of the falling stream and light beams 16 and 18. Outputs from the detectors 20, 22 are fed to data acquisition means 28. Conventional means (not shown) are included to assure a fixed constant rate of water through the cell 12.

Light beam 16 has a wavelength in the ultraviolet or visible portion of the spectrum that stimulates fluorescent emissions, for example, from dissolved and dispersed fluorescent materials in the water stream. The intensity of the fluorescent light resulting from beam 16 is a function primarily of the concentration of fluorescent material in the water sample.

Light beam 18 has a wavelength in the visible or infrared portion of the spectrum, which is so selected so that it does not stimulate fluorescent emissions, but rather is scattered by the suspended particles dispersed in the water sample. The intensity of the scattered light resulting from beam 18 or transmitted light resulting from beam 18 is a function of the suspended particle content of the water sample.

Beams 16 and 18 are focused by optical means 26 such that the width of both beams is smaller than the width of the falling stream 10. This arrangement minimizes the amount of incident beams 16 and 18 that might reflect off the falling stream and enter detectors 20, 22 as stray light. Both the fluorescent emissions and the scattered light are emitted at all angles surrounding the falling stream. Both the fluorescent emissions and the scattered light are selectively detected by detector 20. Detector 20 is configured so that it is not sensitive to the wavelength used in beam 18, but is sensitive to the fluorescent wavelengths stimulated by beam 16 and scattered light at the wavelength of beam 18.

Detector 20 is located at some angle other than 180° to incident beams 16 and 18. The example configuration illustrated in FIG. 1 shows detector 20 at an angle of approximately 90° to the incident beams. This is a preferred angle for optically thin samples, such as drinking water. For highly absorbing or turbid samples, where the incident beams cannot penetrate significantly into the sample, a smaller angle generally yields better results. The optimum angle is selected as determined by the nature of the sample according to spectroscopic guidelines well known in the art.

A second detector 22 is located at 180° to incident beams 16 and 18 to detect the portions of those beams that are transmitted through the falling stream 10. In the presence of turbidity, the transmitted light will be less than the incident light due to scattering by the particulate matter in the stream. Detector 22 is unfiltered so that it is sensitive to the wavelengths of both beams 16 and 18. Detectors 20 and 22 are each configured to separately detect two different wavelengths by either time-division or frequency multiplexing techniques that are well known in the art. Signals from both detectors 20 and 22 are simultaneously collected by data acquisition system 28. The measured light intensities are mathematically combined with appropriate calibration constants to determine the solids and fluorescent materials content of the water stream.

With either time division or frequency multiplexing, detector 22 would be unfiltered so that it is sensitive to the wavelength of both beams 16 and 18. Detector 20 would be configured so that it would not detect the wavelength used in beam 16, but would be sensitive to both the fluorescent wavelengths stimulated by beam 16 and scattered light at the wavelength of beam 18. When using time-division multiplexing, beams 16 and 18 would be alternated in time, so that only one beam hits the water at any given time. When beam 16 is incident on the sample, the signal from detector 20 is proportional to the fluorescent light intensity emitted by the sample. The signal from detector 22 is related to the portion of beam 16 that is transmitted by the sample. When beam 18 is incident on the sample, the signal from detector 20 is proportional to the amount of beam 18 that is scattered into detector 20 by the water sample. The signal from detector 22 is related to the portion of beam 18 that is transmitted by the sample. As an example of one type of frequency multiplexing, beams 16 and 18 would be simultaneously incident on the sample, but would be modulated at different frequencies. To selectively detect fluorescent emissions, the signal from detector 20 would be demodulated at the frequency of beam 16, using, for example, a lock-in amplifier tuned to the frequency of beam 16. To selectively detect scattered light, the signal from detector 20 would be demodulated at the frequency of beam 18. Many other known frequency multiplexing techniques could also be used to separately detect the fluorescent emissions and scattered light.

Simultaneous fluorescence and turbidity measurements are possible using only detector 20, with either time-division or frequency multiplexing as described above. Detector 22 provides additional capabilities by measuring the portions of beams 16 and/or 18 that are transmitted through the sample. The intensities of these transmitted beams can be used to determine the concentrations of components in the sample according to the Beer-Lambert absorption law, which is well known in the art. Therefore, the addition of detector 22 allows Beer-Lambert absorption measurements to be made on the falling stream at the same time the fluorescence and turbidity measurements are made by detector 20. In addition, the turbidity signal from detector 22 can be combined with the simultaneous transmission signal from detector 20 to eliminate turbidity interferences from color, as is well known in the art.

The present invention could be configured with many incident beam arrangements with the two wavelengths used for the measurements separated in time and/or space, as long as all the incident beams illuminate essentially the same portion of the falling stream. The light beams could originate from two separate single-wavelength sources or from a single dual-wavelength source. Light from the sources could be brought to the falling stream using conventional optics (lenses, mirrors, beamsplitters, etc.), fiber optics, or a combination of conventional optics and fiber optics. Detectors 20 and 22 could be of any type, as long as the parameters of geometry, sensitivity, selectivity, spectral range and response time are compatible with the light sources used and the sample to be analyzed. All of these light beam arrangements and detector selection criteria are well known in the art.

A test instrument was constructed incorporating the present invention. A dual-wavelength time-division multiplexing, fiber optic photometer was used to supply the two incident light beams 16 and 18. Beams 16, 18 were generated by two separate xenon flash lamps. Fluorescence emissions and scattered light were detected by a single photomultiplier detector 20. Detector 20 was arranged 90° to incident beams 16 and 18. Beam 16 (fluorescence excitation) had a wavelength such that it excited fluorescence in either a commercially available water soluble corrosion inhibitor or produced oil, depending upon the experiment. Beam 16 fluorescence excitation wavelengths were isolated with narrow bandpass filters in the launch path between the xenon lamps and the fiber optic cables. Emission wavelengths were isolated by broad bandpass filters located in front of the photomultiplier detector. Beam 18 (light scattering) always had a wavelength of 600 nm. For the laboratory experiments a pump was used to continuously circulate a fixed volume of water through the falling stream sampler. This water was either water from an oil field or deionized water. In the experiments carried out in the field, a side stream was used from a produced water line (a once through system). Fluorescence and turbidity responses were measured as various chemical substances were added to the water.

To investigate the instrument's response to fluorescence in the absence of turbidity, fluorescence response was measured as known aliquots of a water dispersable corrosion inhibitor were sequentially added to the circulating water system, which consisted of produced water from an oil field. For this test, the excitation wavelength was 380 nm and the emission wavelength range was 425–650 nm. A calibration curve was constructed by plotting the corrosion inhibitor concentration versus fluorescence response. The resulting curve was linear from 0 to 7 ppm. The intercept was not zero due to the presence of naturally occurring fluorescent substances in the oil field produced water. A linear least squares fit through the measured data gave a correlation coefficient (R squared) of 0.9997.

In another experiment, the instrument's turbidity response was measured in the absence of fluorescence. Aliquots of barium chloride were sequentially added to the circulating water system using oil field produced water, which contained an excess of sodium sulfate. This resulted in the formation of increasing levels of suspended barium sulfate particles. After each barium chloride addition, a small sample was removed and its turbidity was measured with a laboratory turbidimeter (Ratio XR Turbidimeter, HACH Company, Loveland, Colo.). A calibration curve was constructed by plotting the measured turbidity of the sample versus the test instrument's turbidity response. The resulting calibration curve was linear up to 240 NTU. The intercept was not zero due to the apparent turbidity caused by the turbulent surface of the falling stream itself. A linear least squares fit through the measured data gave a correlation coefficient (R squared) of 0.9995.

An experiment was carried out to determine the effect of sample fluorescence on turbidity response. In this experiment the excitation wavelength was 490 nm and the emission wavelength range was 515–700 nm. Barium chloride was added to a circulating sodium sulfate solution to give a barium sulfate turbidity of 200 NTU measured with a laboratory turbidimeter. Fluorescence was then added stepwise by adding sequential aliquots of a completely water soluble fluorescent material (PYLA-TEL Fluorescent Yellow dye,Pylam Garden City, N.Y.). Results showed that the turbidity response was completely independent of added dye over the dye concentration investigated (up to 10 ppm). When a water dispersable (not completely soluble) fluorescent material was used, there was a concomitant increase in turbidity, as would be expected.

A final laboratory experiment was carried out to determine the effect of sample turbidity on fluorescence response. For this experiment the excitation was 380 nm and the emission wavelength range was 425–650 nm. A deionized water sample was made fluorescent by the addition of a water dispersable corrosion inhibitor. An excess of sodium sulfate was added to the fluorescent solution. Aliquots of barium chloride were then added successively to produce increasing levels of barium sulfate turbidity. After each aliquot, a sample was taken and the turbidity was measured with the laboratory turbidimeter. Results showed that fluorescence response increased 9.6% as turbidity increased from 80 to 240 NTU. A plot of fluorescence response versus turbidity response showed that the turbidity effect on fluorescence could be fit with a second order polynomial. Subsequent experiments carried out in the same manner showed that the effect was repeatable, allowing the polynomial function to be used to quantitatively correct the fluorescence response for the presence of turbidity.

It should be noted that in instruments known from the prior art, turbidity affects the measurement of fluorescence. The present invention can compensate for the effect of turbidity on the fluorescence measurement by using the turbidity measurement (measured by transmitted light or scattered light) to correct the fluorescence measurement for turbidity.

Under actual field conditions an experiment was carried out to determine a calibration for turbidity. In this experiment, an aqueous solution of barium chloride was pumped into the produced water stream using a peristaltic pump (Harvard Apparatus,South Natic, Mass.). This produced water stream was already high in sulfate. The barium and sulfate ions produced a water insoluble barium sulfate precipitate, which provided the turbidity in the system. The amount of turbidity formed could be controlled by increasing or decreasing the flow rate of the peristaltic pump. Higher flow rates gave increased turbidity, lower flow rates gave lower turbidity. After each flow rate adjustment, a small sample was removed and its turbidity was measured with a laboratory turbidimeter (Ratio XR Turbidimeter, HACH Company, Loveland, Colo.). A calibration curve was constructed by plotting the measured turbidity of the samples versus the test instrument's turbidity response. The resulting calibration curve was linear up to 100 NTU. The intercept was not zero due to the apparent turbidity caused by the turbulent surface of the stream itself. A linear least squares fit through the measured data gave a correlation coefficient (R squared) of 0.963. This R squared value is slightly lower than for the laboratory derived calibration curve. The reason for this is two-fold. In an actual field system (once through rather than recirculating) there are natural fluctuations that occur in the turbidity of oil field produced water; also there is some error in timing the instrument reading with obtaining a sample for measurement in the HACH instrument. Due to the dynamic nature of the actual field system, a very slight difference in sampling times (HACH instrument versus this invention) can make significant differences in readings.

In a separate experiment, carried out under actual field conditions, a calibration curve was determined for produced oil in the system. Excitation 410 nm, emission 425–650 nm. In this case, the oil measurements for the calibration curve were determined by the HACH oil in water calorimetric extraction method (HACH DR 2000 Method #410). A calibration Curve was constructed by plotting oil concentration versus the test instrument's fluorescence response. The calibration curve was linear up to 1.4 ppm of oil. A least squares fit through the measured data gave a correlation coefficient (R squared) of=0.872. As in the case of the least squares fit for the field turbidity calibration curve, the fact that the correlation coefficient (R squared) for the field calibration curve is lower than a laboratory derived curve is explained by sampling. Due to the dynamic nature of the actual field system, a very slight difference in sampling times (HACH instrument versus this invention) can make significant differences in readings.

In order to simplify calibration (or recalibration after the initial installation) of the instrument, a secondary standard can be used. A calibration curve was determined for a water soluble corrosion inhibitor under actual field conditions. A linear least squares fit through the measured data points had a correlation coefficient (R squared) of 0.994. By using the calibration curve determined in the field for the water soluble corrosion inhibitor and the calibration curve that was determined using actual oil measurements in the field (using the HACH calorimetric test) it was possible to correlate the concentration (ppm) of the water soluble corrosion inhibitor to the concentration of oil. For subsequent calibrations of the instrument, the water soluble corrosion inhibitor can be used instead of oil measurements determined by the HACH method to calibrate the instrument. An example of the benefit of this type of calibration (or calibration check) would be on unmanned offshore platform. The calibration of the instrument could be checked by an addition of corrosion inhibitor, without the necessity of doing the HACH method extractions.

Figure 2:
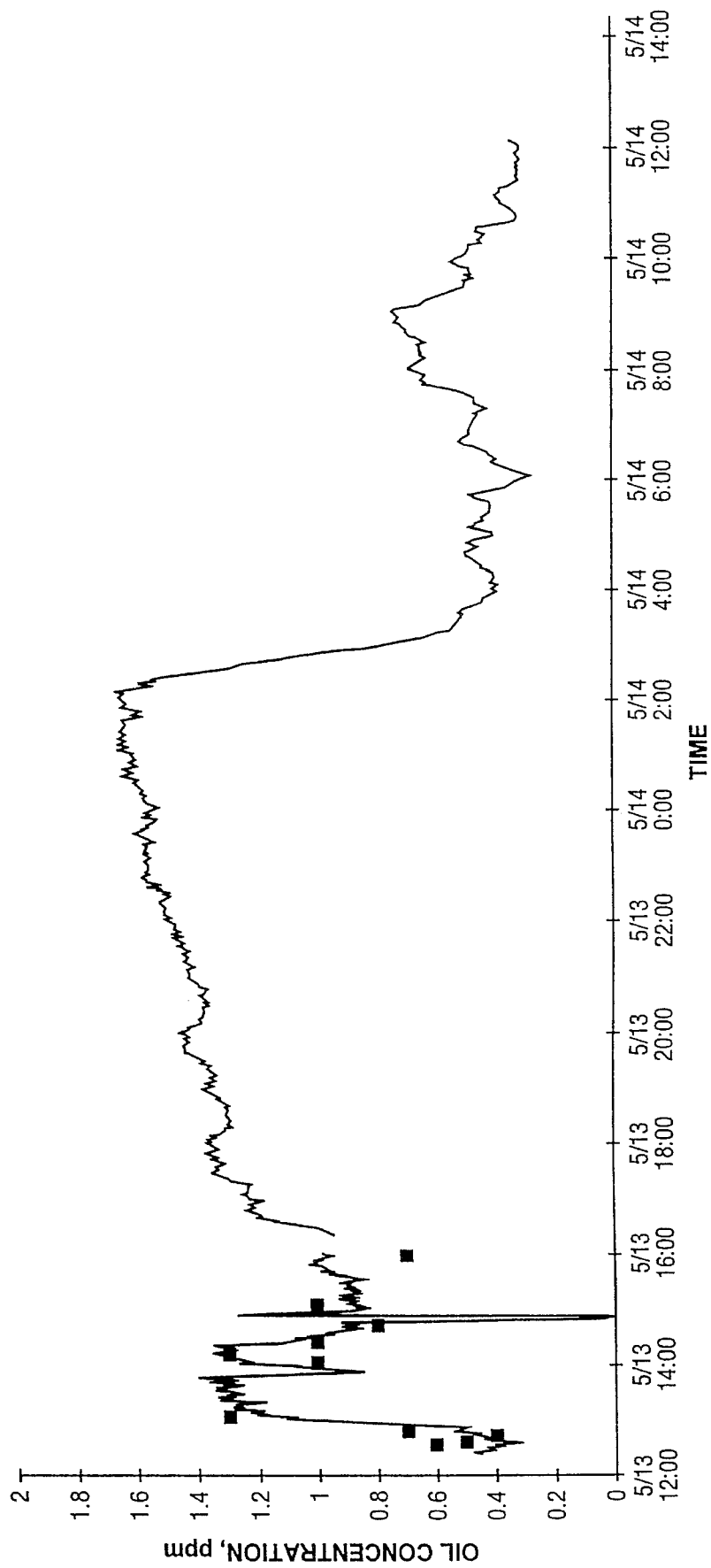
FIG. 2 is a graph of actual field data collected with the instrument according to the present invention.

FIG. 2 is shows the results from using the subject instrument in an actual field setting. In the first part of the graph it can be seen that the oil concentration determined by the HACH method correlates very closely with the readings from the subject instrument. When the water clarifier pump broke (a piece of equipment at the field location which injects a chemical which helps to reduce the oil content of the water) the oil readings from the instrument increased. When the water clarifier pump was repaired and the chemical injected again, the instrument readings for oil content decreased, as would be expected.

The preceding experiments show that the test embodiment built according to the present invention gave linear response to both fluorescence and turbidity. The results also show that turbidity response was independent of fluorescence over the range investigated. Finally, the results show that turbidity had a small effect on fluorescence response, and that the turbidity response could be used to correct for this effect. The ability to correct fluorescence measurements for such turbidity effects is unknown in the prior art.

The present invention would be useful for the detection of many types of fluorescent materials which are foreign to pure water. These include, but are not limited to, aromatic hydrocarbons, corrosion inhibitors, pesticides, human or animal wastes, etc. The ability to correct fluorescence response for presence of turbidity, makes this invention especially suited to the analysis of optically dense and turbid water samples (e.g., river water containing silt and oil field waters containing dispersed suspended particles such as clays, iron sulfide, iron oxide, bacteria, etc.) The invention will also be useful for measuring turbidity from many sources including, but not limited to dispersed hydrocarbons, biomass, debris, and any other water insoluble but water dispersed materials.

The present invention is especially suited, but not limited to, the analysis of oil field waters, which often contain fluorescent dispersed and dissolved hydrocarbons, as well as a wide variety of non-fluorescent suspended solids. It is often permitted to discharge oil field waters to natural water systems as long as the hydrocarbon content is low, even if the dispersed solids content is high. Both of these substances can be simultaneously determined by application of the present invention. Also, since the present invention is not susceptible to fouling, it provides a trouble-free means for reliable, long-term monitoring.

The present invention may be subject to many modifications and changes without departing from the spirit or essential character thereof. The present description should therefore be considered in all respects as being illustrative rather than restrictive of the scope of the invention.

We claim:

1. A method for monitoring the concentration of solids and fluorescent materials in waste water comprising the steps of:

forming a falling stream of waste water;

directing a first beam of light through said falling stream of waste water at approximately right angles to its falling;

directing a second beam of light through said falling stream of waste water parallel to said first beam of light;

measuring fluorescent emission stimulated by said first beam of light; and measuring the light scattered at approximately right angles from the direction of said first and second beams of light whereby both the fluorescence and turbidity of said falling stream of waste water are measured so that said fluorescence measurements are corrected for the effects of turbidity by utilizing a predetermined relationship of fluorescence versus turbidity.

2. A method according to claim 1 wherein said first beam of light is in the ultraviolet or visible portion of the spectrum; and said second beam of light is in the visible or infrared portion of the spectrum.

3. A method according to claim 1 wherein said first beam is of a first wavelength range suitable for stimulating fluorescence from the stream of water; and said second beam is of a second wavelength range suitable for scattering by the stream of water where the shortest wavelength of said second wavelength range is equal to or greater than the shortest fluorescence wavelength to be detected.

4. A method according to claim 1 wherein
a single photodetector, by time-division multiplexing, separately detects fluorescent emissions and scattered light.

5. A method according to claim 1 wherein a single photodetector, by frequency multiplexing, separately detects fluorescent emissions and scattered light.

6. A method according to claim 1 wherein a single multi-wavelength detector separately detects fluorescent emissions and scattered light.

7. A method of monitoring the concentration of solids and fluorescent material in waste water comprising the steps of:
    forming a falling stream of waste water to be monitored;
    directing a single beam of light through said falling stream of waste water wherein said single beam is comprised of both a first wavelength range suitable for stimulating fluorescence from the waste water sample and a second wavelength range suitable for scattering by the waste water sample where the shortest wavelength of said second wavelength range is not less than the shortest fluorescence wavelength to be detected; and
    providing a single detector approximately at right angles to the direction of said beam of light to monitor the intensity of said first and second wavelength ranges whereby both the fluorescence and turbidity of said waste water are measured so that said fluorescence measurements are corrected for the effects of turbidity by utilizing a calculation of fluorescence versus turbidity.

8. A method for monitoring the construction of solids and fluorescent materials in waste water comprising the steps of:
    forming a falling stream of waste water;
    directing a first beam of light through said falling stream of waste water;
    directing a second beam of light through said falling stream of waste water;
    measuring fluorescent emission stimulated by said first beam of light;
    measuring the light scattered at approximately right angles from the beam direction from said second beam of light to ascertain both the fluorescence and turbidity of said waste water; and
    measuring the light passing through the falling steam of waste water so that both the fluorescence and the turbidity are measured and that said fluorescence measurements are corrected for the affects of turbidity by utilizing a calculation of fluorescence versus turbidity.

9. A method according to claim 8 wherein said first beam of light is in the ultraviolet or visible portion of the spectrum; and
    said second beam of light is in the visible or infrared portion of the spectrum.

10. A method according to claim 8 wherein said first beam is of a first wavelength range suitable for stimulating fluorescence from the water sample; and
    said second beam is of a second wavelength range suitable for scattering by the water sample where the shortest wavelength of said second wavelength range is equal to or greater than the shortest fluorescence wavelength to be detected.

11. A method according to claim 8 wherein said measuring steps are carried out by providing:
    a single photodetector means using time-division multiplexing for separately detecting fluorescent emissions and scattered light.

12. A method according to claim 8 wherein said measuring steps are carried out by providing:
    a single photodetector means, using frequency multiplexing for separately detecting fluorescent emissions, and scattered light.

13. A method according to claim 8 wherein said measuring steps are carried out by providing:
    a single multi-wavelength detector means for separately detecting fluorescent emissions and scattered light.

14. An apparatus for monitoring the concentration of solids and fluorescent materials in waste water comprising:
    means forming a falling stream of waste water to be monitored;
    means generating and directing a first beam of light through said falling stream of waste water;
    means generating and directing a second beam of light through said falling stream of waste water;
    means detecting and measuring fluorescent emissions from said falling stream of waste water stimulated by said first beam of light; and
    means detecting and measuring the light scattered at approximately right angles from said falling stream of waste water by said second beam of light whereby both the fluorescence and turbidity of said falling stream of waste water are measured so that said fluorescence measurements are corrected for the effects of turbidity by utilizing a calculation of fluorescence versus turbidity.

15. An apparatus according to claim 14 wherein: said first beam of light is in the ultraviolet or visible portion of the spectrum; and
    said second beam of light is in the visible or infrared portion of the spectrum.

16. An apparatus according to claim 14 wherein:
    said first beam is of a first wavelength range suitable for stimulating fluorescence from the stream of waste water; and
    said second beam is of a second wavelength range suitable for scattering by the stream of waste water where the shortest wavelength of said second wavelength range is equal to or greater than the shortest fluorescence wavelength to be detected.

17. An apparatus according to claim 14 wherein: a single photodetector separately detects and measures the fluorescent emissions and scattered light by time-division multiplexing.

18. An apparatus according to claim 14 wherein: a single photodetector separately detects and measures the fluorescent emissions and scattered light by frequency multiplexing.

19. An apparatus according to claim 14 wherein: a single multi-wavelength detector separately detects and measures the fluorescent emissions and scattered light.

20. An apparatus for monitoring the concentration of solids and fluorescent material in a falling stream of water comprising:
    means forming a falling stream of water to be monitored;
    means generating and directing a single beam of light through said falling stream of water wherein said single beam is comprised of both a first wavelength range suitable for stimulating fluorescence from the water sample and a second wavelength range suitable for scattering by the water sample where the shortest wavelength of said second wavelength range is not less than the shortest fluorescence wavelength to be detected; and detector means to selectively monitor the intensity of selected wavelengths at approximately right angles whereby both the fluorescence and turbidity of said water are measured so that said fluorescence measurements are corrected for the effects of turbidity by utilizing a calculation of fluorescence versus turbidity.

21. An apparatus according to claim 20 wherein said first wavelength range is suitable for stimulating fluorescence from the water sample; and said second wavelength range is suitable for scattering by the water sample where the shortest wavelength of said second wavelength range is equal to or greater than the shortest fluorescence wavelength to be detected.

22. An apparatus according to claim 20 wherein said detector means comprises a single photodetector using time-division multiplexing for separately detecting fluorescent emissions and scattered light.

23. An apparatus according to claim 20 wherein said detector means comprises:

a single photodetector using frequency multiplexing for separately detecting fluorescent emissions and scattered light.

24. An apparatus according to claim 20 wherein said detector means comprises:

a single multi-wavelength detector for separately detecting fluorescent emissions and scattered light.

\* \* \* \* \*